(12) United States Patent
Zhang et al.

(10) Patent No.: US 8,109,879 B2
(45) Date of Patent: Feb. 7, 2012

(54) ASSESSING AUTONOMIC ACTIVITY USING BAROREFLEX ANALYSIS

(75) Inventors: Yunlong Zhang, Mounds View, MN (US); Mark Schwartz, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1342 days.

(21) Appl. No.: 11/329,346

(22) Filed: Jan. 10, 2006

(65) Prior Publication Data

US 2007/0161912 A1    Jul. 12, 2007

(51) Int. Cl.
*A61B 5/00* (2006.01)
(52) U.S. Cl. .......................... 600/483; 600/300; 600/485
(58) Field of Classification Search ................ 600/309, 600/483, 485
See application file for complete search history.

(56) References Cited

U.S. PATENT DOCUMENTS

| | | |
|---|---|---|
| 3,522,811 A | 8/1970 | Wingrove et al. |
| 3,645,267 A | 2/1972 | Hagfors |
| 3,650,277 A | 3/1972 | Sjostrand et al. |
| 3,835,864 A | 9/1974 | Rasor et al. |
| 3,870,051 A | 3/1975 | Brindley |
| 3,943,936 A | 3/1976 | Rasor et al. |
| 4,014,318 A | 3/1977 | Dockum et al. |
| RE30,366 E | 8/1980 | Rasor et al. |
| 4,256,094 A | 3/1981 | Kapp et al. |
| 4,323,073 A | 4/1982 | Ferris |
| 4,331,157 A | 5/1982 | Keller, Jr. et al. |
| 4,481,953 A | 11/1984 | Gold et al. |
| 4,525,074 A | 6/1985 | Murakami |
| 4,531,943 A | 7/1985 | Van Tassel et al. |
| 4,551,862 A | 11/1985 | Haber |
| 4,573,481 A | 3/1986 | Bullara |
| 4,586,501 A | 5/1986 | Claracq |
| 4,590,946 A | 5/1986 | Loeb et al. |
| 4,640,286 A | 2/1987 | Thomson |
| 4,641,664 A | 2/1987 | Botvidsson |
| 4,664,120 A | 5/1987 | Hess |
| 4,682,583 A | 7/1987 | Burton et al. |
| 4,702,254 A | 10/1987 | Zabara |
| 4,709,690 A | 12/1987 | Haber |
| 4,719,921 A | 1/1988 | Chirife |
| 4,739,762 A | 4/1988 | Palmaz |
| 4,762,130 A | 8/1988 | Fogarty et al. |

(Continued)

FOREIGN PATENT DOCUMENTS

WO    WO 97/18856    5/1997

(Continued)

OTHER PUBLICATIONS

Böck et al., Fine structure of baroreceptor terminals in the carotid sinus of guinea pigs & mice, Cell & Tissue Research, 170, pp. 95-112, 1976. Abstract only.

(Continued)

*Primary Examiner* — Charles A Marmor, II
*Assistant Examiner* — Karen Toth
(74) *Attorney, Agent, or Firm* — Hollingsworth & Funk, LLC

(57) ABSTRACT

A method involves implantably detecting changes in posture of a patient's body. Baroreflex responses to the posture changes are determined. An autonomic tone of the patient is determined based on the baroreflex responses. Based on the autonomic tone, various patient susceptibilities to disease may be determined, including susceptibilities to heart disease, arrhythmia, and/or sudden cardiac death.

20 Claims, 10 Drawing Sheets

U.S. PATENT DOCUMENTS

| | | | |
|---|---|---|---|
| 4,762,820 A | 8/1988 | Gavras | |
| 4,770,177 A | 9/1988 | Schroeppel | |
| 4,791,931 A | 12/1988 | Slate | |
| 4,800,882 A | 1/1989 | Gianturco | |
| 4,803,988 A | 2/1989 | Thomson | |
| 4,813,418 A | 3/1989 | Harris | |
| 4,819,662 A | 4/1989 | Heil et al. | |
| 4,825,871 A | 5/1989 | Cansell | |
| 4,828,544 A | 5/1989 | Lane et al. | |
| 4,830,003 A | 5/1989 | Wolff et al. | |
| 4,860,751 A | 8/1989 | Callaghan | |
| 4,867,164 A | 9/1989 | Zabara | |
| 4,881,939 A | 11/1989 | Newman | |
| 4,886,062 A | 12/1989 | Wiktor | |
| 4,887,608 A | 12/1989 | Mohl et al. | |
| 4,917,092 A | 4/1990 | Todd et al. | |
| 4,960,129 A | 10/1990 | dePaola et al. | |
| 4,960,133 A | 10/1990 | Hewson | |
| 4,969,458 A | 11/1990 | Wiktor | |
| 4,972,848 A | 11/1990 | DiDomenico | |
| 5,010,893 A * | 4/1991 | Sholder | 600/595 |
| 5,025,807 A | 6/1991 | Zabara | |
| 5,040,533 A | 8/1991 | Fearnot | |
| 5,042,497 A * | 8/1991 | Shapland | 600/509 |
| 5,078,736 A | 1/1992 | Behl | |
| 5,113,869 A | 5/1992 | Nappholz et al. | |
| 5,117,826 A | 6/1992 | Bartelt et al. | |
| 5,144,960 A | 9/1992 | Mehra et al. | |
| 5,170,802 A | 12/1992 | Mehra | |
| 5,181,911 A | 1/1993 | Shturman | |
| 5,199,428 A | 4/1993 | Obel et al. | |
| 5,203,326 A | 4/1993 | Collins | |
| 5,215,089 A | 6/1993 | Baker, Jr. | |
| 5,222,971 A | 6/1993 | Willard et al. | |
| 5,224,491 A | 7/1993 | Mehra | |
| 5,259,394 A | 11/1993 | Bens | |
| 5,282,468 A | 2/1994 | Klepinski | |
| 5,295,959 A | 3/1994 | Gurbel et al. | |
| 5,299,569 A | 4/1994 | Wernicke et al. | |
| 5,304,206 A | 4/1994 | Baker, Jr. et al. | |
| 5,314,453 A | 5/1994 | Jeutter | |
| 5,318,592 A | 6/1994 | Schaldach | |
| 5,330,507 A | 7/1994 | Schwartz | |
| 5,330,515 A | 7/1994 | Rutecki et al. | |
| 5,351,394 A | 10/1994 | Weinberg | |
| 5,409,009 A | 4/1995 | Olson | |
| 5,411,540 A | 5/1995 | Edell et al. | |
| 5,437,285 A | 8/1995 | Verrier et al. | |
| 5,458,626 A | 10/1995 | Krause | |
| 5,509,888 A | 4/1996 | Miller | |
| 5,522,854 A | 6/1996 | Ideker et al. | |
| 5,529,067 A | 6/1996 | Larsen et al. | |
| 5,531,779 A | 7/1996 | Dahl et al. | |
| 5,535,752 A | 7/1996 | Halperin et al. | |
| 5,540,734 A | 7/1996 | Zabara | |
| 5,540,735 A | 7/1996 | Wingrove | |
| 5,545,132 A | 8/1996 | Fagan et al. | |
| 5,545,202 A | 8/1996 | Dahl et al. | |
| 5,571,150 A | 11/1996 | Wernicke et al. | |
| 5,575,809 A | 11/1996 | Sasaki | |
| 5,578,061 A | 11/1996 | Stroetmann et al. | |
| 5,634,878 A | 6/1997 | Grundei et al. | |
| 5,643,330 A | 7/1997 | Holsheimer et al. | |
| 5,645,570 A | 7/1997 | Corbucci | |
| 5,651,378 A | 7/1997 | Matheny et al. | |
| 5,682,901 A | 11/1997 | Kamen | |
| 5,690,681 A | 11/1997 | Geddes et al. | |
| 5,692,882 A | 12/1997 | Bozeman, Jr. et al. | |
| 5,695,468 A | 12/1997 | Lafontaine et al. | |
| 5,700,282 A | 12/1997 | Zabara | |
| 5,707,400 A | 1/1998 | Terry, Jr. et al. | |
| 5,715,837 A | 2/1998 | Chen | |
| 5,725,471 A | 3/1998 | Davey et al. | |
| 5,725,563 A | 3/1998 | Klotz | |
| 5,727,558 A | 3/1998 | Hakki et al. | |
| 5,741,316 A | 4/1998 | Chen et al. | |
| 5,766,236 A | 6/1998 | Detty et al. | |
| 5,797,840 A * | 8/1998 | Akselrod et al. | 600/301 |
| 5,800,464 A | 9/1998 | Kieval | |
| 5,807,258 A | 9/1998 | Cimochowski et al. | |
| 5,814,079 A | 9/1998 | Kieval | |
| 5,824,021 A | 10/1998 | Rise | |
| 5,861,015 A | 1/1999 | Benja-Athon | |
| 5,876,422 A | 3/1999 | van Groeningen | |
| 5,891,181 A | 4/1999 | Zhu | |
| 5,913,876 A | 6/1999 | Taylor et al. | |
| 5,916,239 A | 6/1999 | Geddes et al. | |
| 5,919,220 A | 7/1999 | Stieglitz et al. | |
| 5,928,272 A * | 7/1999 | Adkins et al. | 607/45 |
| 5,938,596 A | 8/1999 | Woloszko et al. | |
| 5,967,986 A | 10/1999 | Cimochowski et al. | |
| 5,967,989 A | 10/1999 | Cimochowski et al. | |
| 5,987,352 A | 11/1999 | Klein et al. | |
| 5,989,230 A | 11/1999 | Fischell et al. | |
| 6,006,134 A | 12/1999 | Hill et al. | |
| 6,023,642 A | 2/2000 | Shealy et al. | |
| 6,050,952 A | 4/2000 | Hakki et al. | |
| 6,052,623 A | 4/2000 | Fenner et al. | |
| 6,058,331 A | 5/2000 | King | |
| 6,061,596 A | 5/2000 | Richmond et al. | |
| 6,073,048 A | 6/2000 | Kieval et al. | |
| 6,077,227 A | 6/2000 | Miesel et al. | |
| 6,077,298 A | 6/2000 | Tu et al. | |
| 6,110,098 A | 8/2000 | Renirie et al. | |
| 6,161,029 A | 12/2000 | Spreigl et al. | |
| 6,178,349 B1 | 1/2001 | Kieval | |
| 6,206,914 B1 | 3/2001 | Soykan et al. | |
| 6,231,516 B1 | 5/2001 | Keilman et al. | |
| 6,292,695 B1 | 9/2001 | Webster et al. | |
| 6,292,703 B1 | 9/2001 | Meier et al. | |
| 6,356,788 B2 | 3/2002 | Boveja | |
| 6,393,324 B2 | 5/2002 | Gruzdowich et al. | |
| 6,438,409 B1 * | 8/2002 | Malik et al. | 600/512 |
| 6,438,428 B1 | 8/2002 | Axelgaard et al. | |
| 6,473,644 B1 | 10/2002 | Terry et al. | |
| 6,522,926 B1 | 2/2003 | Kieval et al. | |
| 6,564,101 B1 | 5/2003 | Zikria | |
| 6,600,956 B2 | 7/2003 | Maschino | |
| 6,622,041 B2 | 9/2003 | Terry et al. | |
| 6,748,272 B2 | 6/2004 | Carlson et al. | |
| 6,827,689 B2 | 12/2004 | Lin | |
| 6,850,801 B2 | 2/2005 | Kieval et al. | |
| 6,926,670 B2 | 8/2005 | Rich et al. | |
| 6,935,344 B1 * | 8/2005 | Aboul-Hosn et al. | 128/898 |
| 6,942,622 B1 * | 9/2005 | Turcott | 600/508 |
| 6,942,686 B1 | 9/2005 | Barbut et al. | |
| 6,985,774 B2 | 1/2006 | Kieval et al. | |
| 7,155,284 B1 | 12/2006 | Whitehurst et al. | |
| 7,158,832 B2 | 1/2007 | Kieval et al. | |
| 7,194,313 B2 | 3/2007 | Libbus | |
| 7,218,964 B2 | 5/2007 | Hill et al. | |
| 7,277,761 B2 | 10/2007 | Shelchuk | |
| 7,313,444 B2 | 12/2007 | Pianca et al. | |
| 7,499,742 B2 | 3/2009 | Bolea | |
| 7,509,166 B2 | 3/2009 | Libbus | |
| 2002/0005982 A1 | 1/2002 | Borlinghaus | |
| 2002/0058877 A1* | 5/2002 | Baumann et al. | 600/485 |
| 2002/0068897 A1 | 6/2002 | Jenkins et al. | |
| 2002/0103516 A1 | 8/2002 | Patwardhan et al. | |
| 2002/0151051 A1 | 10/2002 | Li | |
| 2004/0115182 A1* | 6/2004 | Fallon | 424/94.2 |
| 2004/0193231 A1 | 9/2004 | David et al. | |
| 2004/0215263 A1* | 10/2004 | Virag et al. | 607/17 |
| 2005/0149132 A1 | 7/2005 | Libbus | |
| 2005/0149156 A1 | 7/2005 | Libbus et al. | |
| 2006/0058590 A1* | 3/2006 | Shaw et al. | 600/301 |
| 2006/0122522 A1 | 6/2006 | Chavan et al. | |
| 2007/0038278 A1 | 2/2007 | Zarembo | |
| 2007/0088214 A1 | 4/2007 | Shuros et al. | |
| 2008/0171923 A1 | 7/2008 | Bolea et al. | |

FOREIGN PATENT DOCUMENTS

| | | |
|---|---|---|
| WO | WO 99/26530 | 6/1999 |
| WO | WO 99/42039 | 8/1999 |
| WO | WO 99/42176 | 8/1999 |
| WO | WO 01/00273 | 1/2001 |

OTHER PUBLICATIONS

Bolea et al., Preliminary Statement for Assessing Autonomic Activity using Baroreflex Analysis, Oct. 31, 2007, pp. 2.

Brattstrom, Influence of continuous and intermittent (R-Wave Triggered) electrical stimulation of the carotid sinus nerve on the static characteristic of the the circulatory regulator, Experientia 28:414-416, 1972. Abstract only.

Braunwald et al., Carotid sinus stimulation for the treatment of angina pectoris, Official Journal of the CA Medical Assoc., vol. 112, No. 3, pp. 78-79, Mar. 1970.

Coleridge et al., Reflex Effects of Stimulating Baroreceptors in the Pulmonary Artery, J. Physiol., 1963, 166, pp. 197-210.

Ebert et al., Fentanyl-Diazepam Anesthesia with or without now Does Not Attenuate Cardiopulmonary Baroreflex-Mediated Vasoconstrictor Responses to Controlled Hypovolemia in Humans, Anesthesia and Analgesia, 1988, 67(6), pp. 548-554. Abstract only.

Goldberger et al., New technique for vagal nerve stimulation, Journal of Neuroscience Methods, 1999, pp. 109-114. Abstract only.

Hainsworth, Cardiovascular reflexes from ventricular and coronary receptors, Adv. Exp. Med. Biol., 1995, 381:157-75.

Krauhs, Structure of rat aortic baroreceptors & their relationship to connective tissue, Journal of Neurocytology, pp. 401-414, 1979. Abstract only.

Lindblad et al., Circulatory effects of carotid sinus stimulation & changes in blood volume distribution in hypertensive man, Acta. Physiol. Scand, 1981, 111:299-306, Mar. 1981. Abstract only.

McMahon et al., Reflex responses from the main pulmonary artery and bifurcation in anaesthetized dogs, Experimental Physiology, 2000, 85, 4, pp. 411-419.

Nishi et al., Afferent Fibres From Pulmonary Arterial Baroreceptors in the Left Cardiac Sympathetic Nerve of the Cat, j. Physiol. 1974, 240, pp. 53-66.

Peters et al., Cardiovascular response to time delays of electrocardiogram-coupled electrical stimulation of carotid sinus nerves in dogs, Journal of the Autonomic Nervous Systems, 25:173-180, 1988. Abstract only.

Peters et al., The principle of lectrical carotid sinus nerve stimulation: a nerve pacemaker system for angina pectoris and hypertension therapy, Annals of Biomedical Engineering, 8:445-458, 1980.

Richter et al., The course of inhibition of sympathetic activity during various patterns of carotid sinus nerve stimulation, Pflugers Arch., 317:110-123, 1970. Abstract only.

Schauerte et al., Transvenous parasympathetic nerve stimulation in the inferior vena cava and atrioventricular conduction, J Cardiovasc Electrphysiol, Jan. 2000, 11(1):64-69, 1 page. Abstract only.

Sedin, Responses of the cardiovascular system to carotid sinu nerve stimulation, Upsala J Med Sci, 81:1-17, 1976. Abstract only.

Solti et al., Baropacing of the carotid sinus nerve for treatment of intractable hypertension, Zeitschrift Für Kardiologie, band 64, Heft 4, pp. 368-374, 1975. Abstract only.

Tarver et al., Clinical experience with a helical bipolar stimulating lead, PACE, vol. 15, part II, Oct. 1992, pp. 1545-1556. Abstract only.

Warzel et al., Effects of carotis sinus nerve stimulation at different times in the respiratory and cardiac cycles on variability of heart rate and blood pressure of normotensive and renal hypertensive dogs, Journal of the Autonomic Nervous System, 26:121-127, 1989. Abstract only.

Warzel et al., The effect of time of electrical stimulation of the carotid sinus on the amount of reduction in arterial pressure, Pfugers Arch, 337-44, 1972. Abstract only.

Frenneaux MD, Autonomic changes in patients with heart failure and in post-myocardial infarction patients, http://www.bmjjournals.com/cgi/reprintform, Heart 2004, 90:1248-1255.

Sanderson et al., Effect of beta blockade on baroreceptor and autonomic function in heart failure, Clinical Science, 1999, 96:137-146.

Lanfranchi PA and Somers VK, Arterial baroreflex function and cardiovascular variability: interactions and implications, http://www.ajpregu.org, Am J Physiol Integr Comp Physiol. 2002, 283:R815-R826.

LaRovere et al., Short-term heart rate variability strongly predicts sudden cardiac death in chronic heart failure patients, http://www.circulationaha.org, Circulation, 2003, 107:565-570.

Apr. 8, 2010, International Preliminary Report on Patentability dated Apr. 8, 2010 from PCT Application No. PCT/US2008/077492, 9 pages.

Feb. 3, 2009, International Search Report and Written Opinion dated Feb. 3, 2009 from PCT Application No. PCT/US2008/077492, 17 pages.

Apr. 3, 2002, IntraCoil Self-Expanding Peripheral Stent, US FDA, 1 page.

File history for U.S. Appl. No. 11/904,946, 155 pages.

\* cited by examiner

Figure 2B    Figure 2C

ASSESSING AUTONOMIC ACTIVITY USING BAROREFLEX ANALYSIS

FIELD OF THE INVENTION

The present invention relates generally to medical devices, and more particularly to detecting autonomic activities with implantable medical devices.

BACKGROUND OF THE INVENTION

Heart failure is a common public health problem, affecting over 5 million people in the U.S. alone. The annual mortality rate due to heart failure is estimated to be 20-25%. Heart failure is a costly disease, both financially and in loss of life. Recent improvements in the surgical and medical management of heart disease have made it more important that heart disease patients are early and accurately classified into high and low risk groups. By examining indicators that are more indicative of mortality risk, high risk patients can receive more targeted treatment. One set independent mortality indicators for heart failure patients are imbalances in the autonomic nervous system.

The autonomic nervous system is responsible for maintaining a relatively constant internal physiological environment by controlling such involuntary functions as digestion, respiration, perspiration, and metabolism, and by modulating blood pressure. The autonomic nervous system is divided into two subsystems, the sympathetic and the parasympathetic. The sympathetic subsystem is responsible for providing responses and energy needed to cope with stressful situations. In response to such stress, the sympathetic system increases the level of certain autonomic activity including heart rate and blood pressure. The parasympathetic nervous system, in contrast, conserves energy by, for example, slowing the heart rate and increasing intestinal and gland activity. The parasympathetic nervous system acts to reverse the effects of the sympathetic nervous system.

Increased sympathetic and depressed parasympathetic nervous activity is common in heart failure. Autonomic imbalance is suspected of predisposing the heart to chronic ventricular dysfunction. This imbalance may be characterized a marked augmentation of sympathetic drive as well as an attenuation of parasympathetic tone. This disruption of autonomic balance appears to significantly contribute to the vasoconstriction that accompanies ventricular failure. Autonomic imbalance also predisposes the heart to ventricular arrhythmias, therefore is reported to be an independent risk factor for the mortality in heart failure population.

Measuring autonomic activity may useful for many purposes. Accurately detecting and determining the level or degree of heart failure in a patient is a particularly desirable use for such measurements. The present invention describes methods, systems, and apparatuses for assessing autonomic activity. Such assessment can be used, among other things, for early identification of patients with high risk of sudden death to enable early, aggressive intervention, and offers various other advantages over the prior art.

SUMMARY OF THE INVENTION

Embodiments of the invention relate to detection of patient posture. In one embodiment of the invention, a method involves implantably detecting changes in posture of a patient's body. Baroreflex responses to the posture changes are detected, and an autonomic tone of the patient is determined based on the baroreflex responses.

In more particular embodiments, determining baroreflex responses to the posture changes may involve measuring the patient's heart rate and/or blood pressure during time periods corresponding to the changes in posture. Measuring the blood pressure of the patient's body may involve measuring the blood pressure via a force transducer sensitive to displacement of a blood vessel, including at least one of a blood-vessel-implantable stent-like transducer and a cuff transducer placed around a blood vessel. The stent-like transducer may be implanted in a vein that is paralleled by an artery.

In other, more particular embodiments, detecting the change in posture via the implantable device involves detecting the change in posture via at least one of a piezoelectric sensor and a mechanical sensor. Determining the autonomic imbalance of the patient may involve performing a baroreflex sensitivity analysis (BSA) based on blood pressure and cardiac signals measured during a time period corresponding to the posture change. Performing the BSA may involve measuring intervals between heartbeats at least during the time period corresponding to the posture change and/or performing a power spectral analysis on the intervals between the heartbeats (e.g., R-R intervals). In other variations, performing the BSA involves determining a rate of change of systolic blood pressure relative to the intervals during the time period corresponding to the posture change. The method may also involve determining the patient's susceptibility to heart disease, arrhythmia, and/or sudden cardiac death based on the autonomic tone.

In another embodiment of the invention, an apparatus that is capable of being implanted in a patient's body includes a posture sensor, a heart rate sensor, and a processor coupled to the posture sensor and the heart rate sensor. The processor is configured to measure the patient's heart rate via the cardiac signal sensor and detect a change in a posture of the patient's body via the posture sensor. An autonomic tone of the patient's body is determined based on the patient's heart rate measured during a time period corresponding to the change in posture.

In one arrangement, the processor is configured to determine the autonomic tone in a time period that encompasses a first time period before the change in posture and a second time period after the change in posture. The posture sensor may include at least one of a piezoelectric sensor and an accelerometer. In another arrangement, he posture sensor includes a case having a plurality of conductive surfaces disposed on an inner surface of the case and a conductive solid movably disposed along the inner surface of the case. Movement of the conductive solid within the case causes the conductive solid to create an electrical connection between at least two surfaces of the plurality of surfaces.

In another embodiment of the invention, a posture sensing system includes: means for detecting a change in posture of a patient's body; means for measuring the patient's heart rate during at least one of a first time period before the change in posture, a second time period during the change in posture, and a third time period after the change in posture; and means for determining an autonomic tone of the patient based on the heart rate measured during the at least one of the first, second, and third time periods.

The above summary of the invention is not intended to describe each embodiment or every implementation of the invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 2B-D are perspective views illustrating a mechanical posture sensor according to an embodiment of the invention;

Figure 1A:
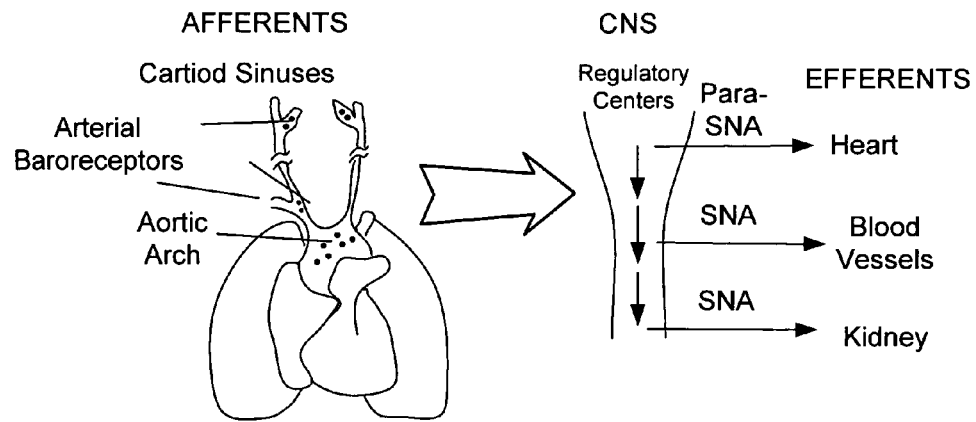
FIG. 1A illustrates afferent and efferent nerve systems that may be used in connection with baroreflex analysis in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

The present invention deals with methods, systems, and devices used to detect imbalances of the autonomic nervous system for purposes of medical treatment. The autonomic nervous system plays a pivotal role in the maintenance of blood pressure. Imbalances of the autonomic nervous system are an independent mortality indicator for heart failure patients and other diseases. Detecting autonomic imbalance may be useful in other applications as well. For example patients with syncope (temporary loss of consciousness and posture) may benefit from an autonomic monitoring device. In another example, measurement of autonomic imbalance may be useful for therapy steering. Autonomic detection could be used in delivering ventricular tachycardia (VT) therapy if heart rhythm is hemodynamically stable, as well as for adjusting heart failure parameters a cardiac rhythm therapy (CRT) device. Therefore, there are many cases where it may be useful to characterize and detect autonomic imbalances.

The detection of autonomic imbalance involves measuring the autonomic response to blood pressure changes that occur when a patient changes posture (e.g., goes from standing to sitting, sitting to lying down, etc.). By measuring various aspects blood pressure and/or heart rate during posture changes, patients with high mortality risk due to autonomic imbalance can be identified and treated appropriately. Using implantable devices to detect autonomic imbalance indicators allows such measurements to be made unobtrusively and long term, and may increase the effectiveness of disease determination and treatment.

The baroreflex test, which measures the autonomic response to blood pressure changes, is one method to measure the autonomic activity. Activation of baroreflex is a major afferent limb of moment-to-moment blood pressure response to physiological or pathophysiological changes. Research has shown that baroreflex is reduced in heart failure and myocardial infarction patients, and is a predictor of the susceptibility to arrhythmias and sudden cardiac death in this population.

The baroreflex (also known as baroreceptor reflex) is the body's rapid response system for dealing with changes in blood pressure. Baroreflex is a reflex triggered by stimulation of a baroreceptor. A baroreceptor includes any sensor of pressure changes, such as afferent nerves, sensory nerve endings in the wall of the atria of the heart, vena cava, aortic arch and/or carotid sinus, etc., that are sensitive to stretching. The baroreflex functions as a negative feedback system. Increased pressure stretches blood vessels, which in turn activates baroreceptors in the vessel walls. Activation of baroreceptors naturally occurs through increasing of the internal pressure and stretching of the arterial wall, causing baroreflex inhibition of sympathetic nerve activity (SNA) and a reduction in systemic arterial pressure. Reduction in blood pressure decreases peripheral vascular resistance and causes respiration to become faster and deeper.

In addition to altering heart rate, baroreflex, through its sympathetic effector branch, also affects resistance of peripheral vascular vessels (e.g., arterioles) and venous compliance. Baroreceptors in the human body detect the pressure of blood flowing though them, and can send messages to the central nervous system to increase or decrease total peripheral resistance and cardiac output. In this way, baroreflex may be responsible for a part of the low frequency component of heart rate variability.

FIG. 1A illustrates neural mechanisms that control the baroreflex phenomena described above. FIG. 1A generally illustrates afferent nerves that convey impulses toward a nerve center. The nerve center detects physiological changes related to the baroreflex. For example, a vasomotor nerve center deals with nerves that dilate and constrict blood vessels to control the size of the blood vessels. FIG. 1A also generally illustrates efferent nerves that convey impulses away from the nerve center. The efferent nerves deliver impulses used to control bodily functions.

Figure 1B:
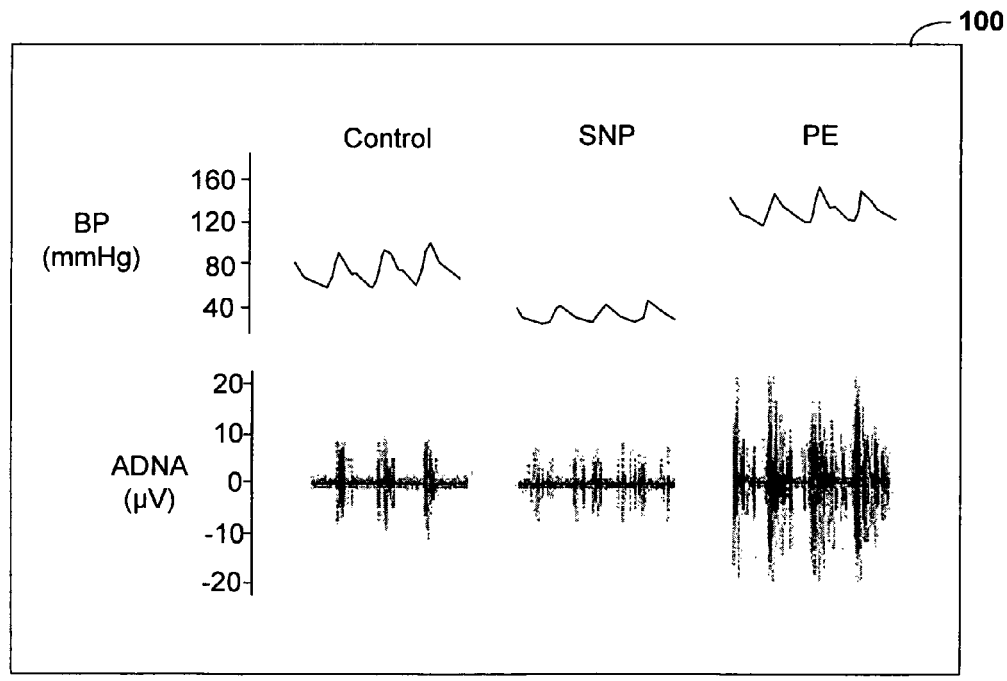
FIG. 1B is a plot illustrating changes in aortic depressor nerve activity changes in arterial pressure that may be used in connection with baroreflex analysis in accordance with embodiments of the invention.

FIG. 1B includes a graph 100 illustrating changes in aortic depressor nerve activity (ADNA) in response to sodium nitroprusside—(SNP) and phenylephrine—(PE) induced changes in arterial pressure. The ADNA activity in response to PE and SNP is typically used to analyze and diagnose baroreflex response. However, the use of SNP and PE to induce blood pressure changes is more suited for a lab environment, and would not be practical for long-term, ambulatory measurements of baroreflex response. More information related to the concepts illustrated in FIGS. 1A and 1B may be found in "Chapter 1: The Baroreceptor Reflex: Novel Methods and Mechanisms," Neural Mechanisms of Cardiovascular Regulation, edited by Dun N. J., Machado B. H., and Pilowsky P. M., Kluwer Academic Publishers, 2004.

Figure 1C:
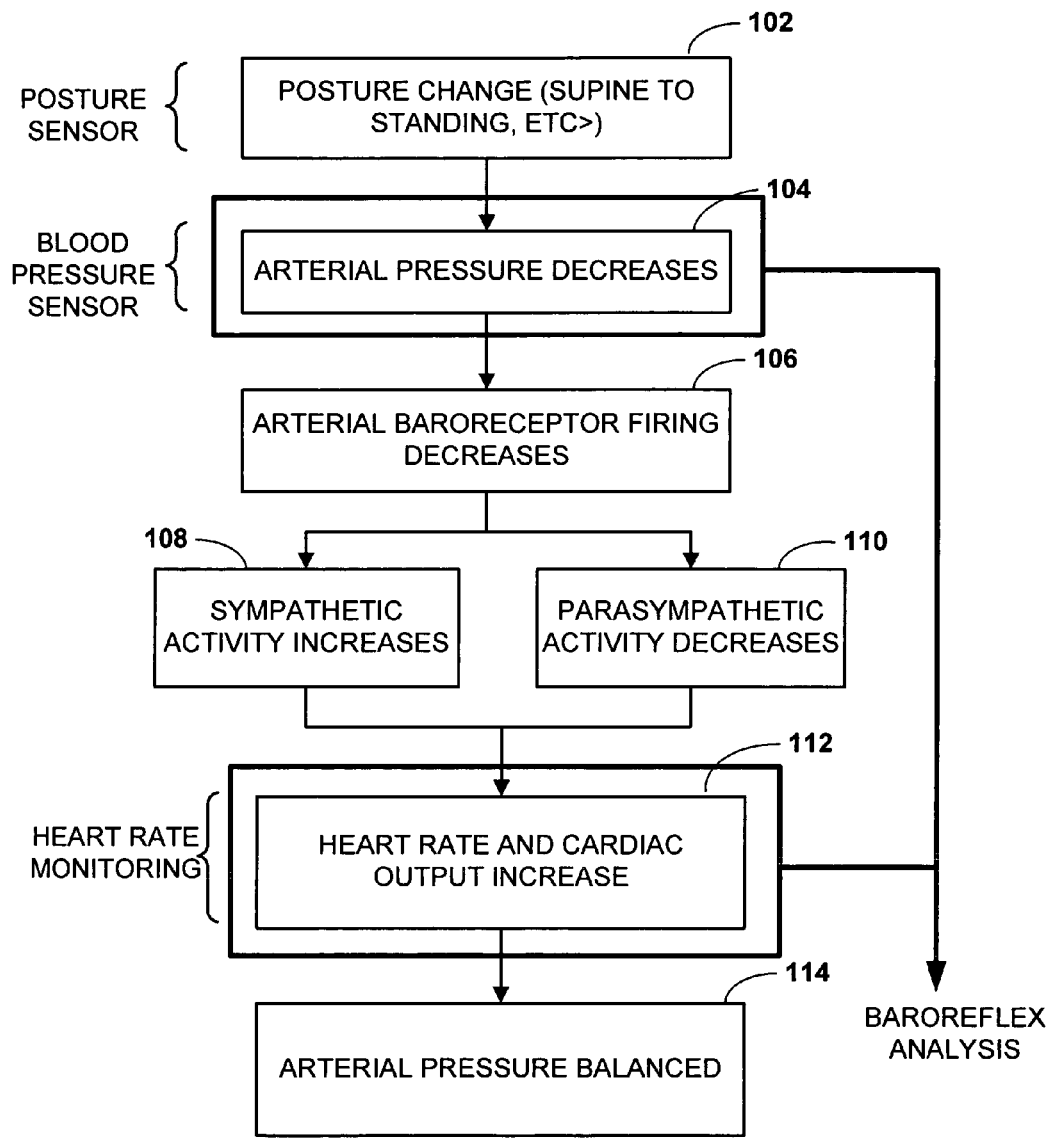
FIG. 1C is a block diagram illustrating the detection of baroreflex activity based on posture change according to an embodiment of the t invention.

In reference now to FIG. 1C, a block diagram illustrates the ambulatory detection of baroreflex activity based on posture change according to an embodiment of the invention. Posture change 102 is a daily activity that could trigger baroreflex. Posture changes 102 (e.g., supine to standing, squat to standing, tilting, etc.) typically results in a pool of blood in the lower limbs and less blood flow to the heart, and thus arterial blood pressure decreases 104. In response, baroreceptor firing decreases 106, thus triggering an increase in sympathetic nerve activity 108 and a decrease in parasympathetic activity 110. In response to the nerve activity 108, 110, the heart rate and cardiac output increase 112, and blood pressure returns to normal 114. Therefore, a medical device capable of detecting baroreflex by way of ambulatory posture and blood pressure measurements could provide important autonomic activity information useful for monitoring patients and subscribing and/or modifying treatments.

Figure 1D:
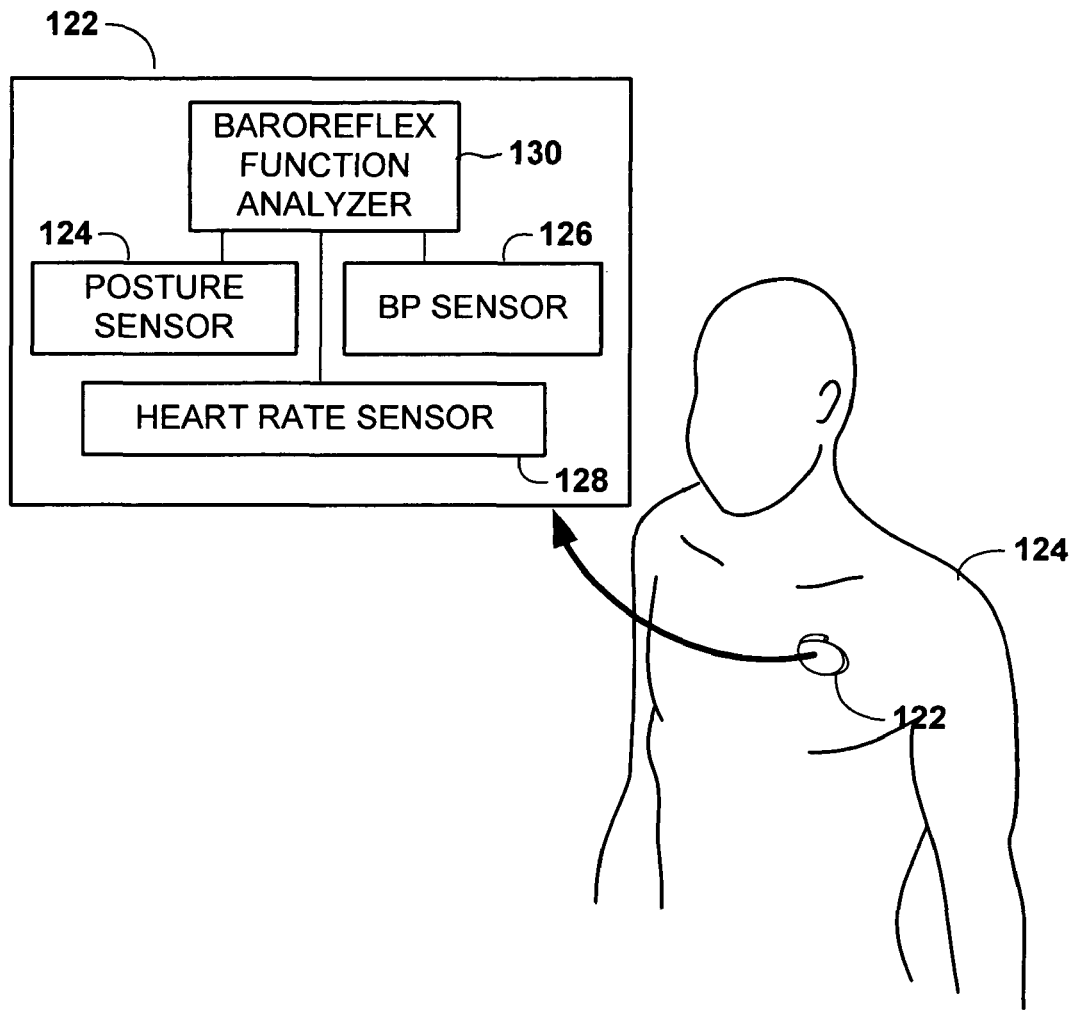
FIG. 1D illustrates an implantable device according to an embodiment of the invention.

In order to obtain long-term, ambulatory measurements of baroreflex and related autonomic indicators, an implantable medical device can be used. FIG. 1D illustrates an implantable medical device 122 according to embodiments of the present invention. The medical device 122 incorporates a posture detector according to an embodiment of the invention. The device 122 may be implanted within a patient's body 124 in the upper left thoracic region, such as a typical placement for a cardiac pacemaker or defibrillator. The medical device 122 includes hardware and software capable of accurately measuring baroreflex. In particular, the medical device 122 may contain any combination of a posture sensor 124, a blood pressure sensor 126, and a heart rate sensor 128. The sensors 124, 126, 128 may be self contained within the medical device 122, and/or work in conjunction with an external apparatus that provides sensory inputs. For example, the heart rate sensor 126 may be coupled an electrode contained in intracardiac leads, where the electrode detects the electrical signals that the heart rate sensor 126 uses to determine heart rate.

The posture detector 124 may be contained within the medical device, and detect posture indirectly by detecting the orientation of the device 122 itself. The term posture as used herein generally refers to the orientation of the patient's torso relative to the earth's surface. In some cases, an absolute measurement of current posture may not be required to measure baroreflex. For example, it may sufficient for the posture detector 124 to sense only relative changes in posture (e.g., detecting rotation) in order determine baroreflex triggers. In other arrangements, it may be desirable for the posture detector 124 to sense absolute orientations of the body (e.g., standing, supine, etc.). Some sequences of posture orientations and changes may be more likely to trigger baroreflex indicators than others. For example, standing after being in a supine position for a long period may be more likely to trigger measurable baroreflex activity than other posture changes.

In response to posture changes detected by the posture detector 124, the blood pressure detector 126 and heart rate sensors 128, the device 122 will make continuous, beat-to-beat readings of blood pressure and cardiac electrical signals. These blood pressure and heart rate readings are analyzed by a baroreflex function analyzer 130. The baroreflex function analyzer 130 continuously monitors outputs of the posture, blood pressure, and heart rate sensors 124, 126, 128 and makes determinations of autonomic imbalance as determined by baroreflex indicators.

Figure 2A:
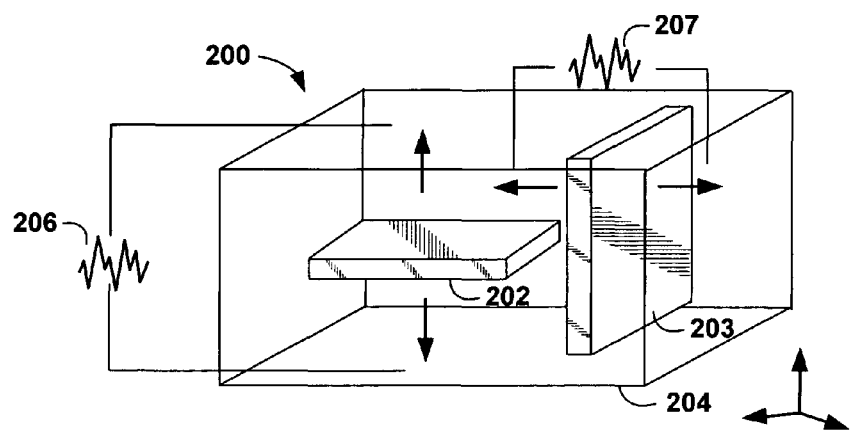
FIG. 2A is a perspective view illustrating a posture sensing element according to an embodiment of the invention.

In reference now to FIG. 2A, an example embodiment of a sensor 200 used for posture detecting is illustrated. The sensor 200 includes a multiple-dimensional piezoelectric element 202. One or more elements 202, 203 are contained in a case 204 where the elements 202, 203 may deflect in response to motion. A deflection of the elements 202, 203 generates a voltage that is proportional to the deflection and is detected by circuitry (not shown) as electrical signals 206, 207.

The illustrated sensor 200 may be configured, for example, as a custom or off-the shelf device, such as a piezoelectric accelerometer. Alternate configurations of the sensor 200 may include any sensor technology that is responsive to gravitational fields and/or motion. One example of a gravitational field sensor is a DC accelerometer, and an example of a motion sensor is an AC accelerometer. Generally, a DC accelerometer refers to a device that can measure static acceleration (i.e., 0 Hz events). For example, capacitive accelerometers are capable of measuring static acceleration. In contrast, AC accelerometers generally cannot measure static events; they need motion to provide an output. The output of AC accelerometers usually decrease as the change in acceleration approaches zero.

Figure 2D:
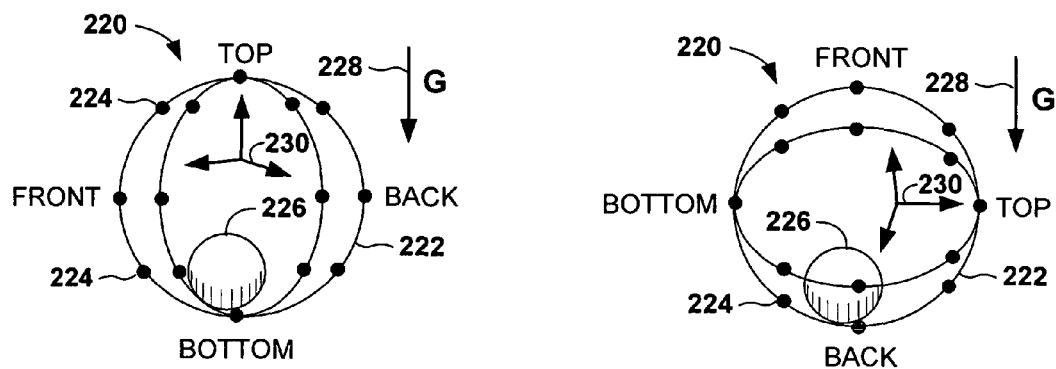
Figure 2D:
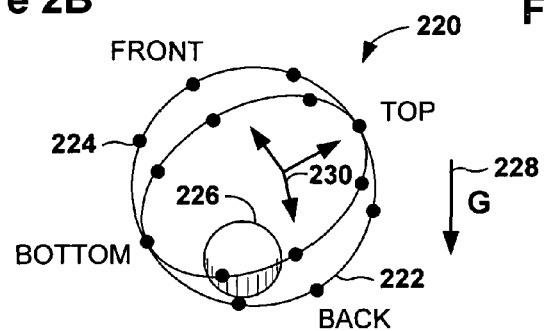

An alternative to using solid state devices such as the piezoelectric element 202 is to use mechanical devices. FIGS. 2B-D illustrate a mechanical posture sensor 220 according to an embodiment of the invention. The sensor 220 includes a wired case ball 222 with a plurality of electrodes 224 (or other conductive surfaces) spaced around an inner surface of the case 222. A small conducting ball 226 is able to move about freely along the inner surface of the case ball 222. The ball 226 tends to roll to the bottom of the case 222 due to the effect of gravity, represented by the gravitational vector G 228. The ball 226 completes a circuit between two or more electrodes 224, and current flowing through the circuit(s) can be used as input to a circuit that determines orientation. The sensitivity and resolution of the sensor 220 is generally dependent on the number and spacing of electrodes 224.

The sensor 220 has an internal coordinate system 230 that may be aligned with the patient's body. The sensor 220 detects posture changes by detecting which electrodes are 224 touched by the ball 226 in different orientations. Therefore, based on a predetermined orientation of the internal coordinate system 230 with the patient's body (e.g., the torso), the orientation of the patient can be determined based on current flowing through electrodes 224.

The top, bottom, front, and back labels in FIGS. 2B-D indicate the orientation of the case ball 222 relative to the patient's body. Thus the orientation shown in FIG. 2B may correspond to a standing posture, the orientation in FIG. 2C may correspond to a supine posture, and the orientation shown in FIG. 2D may correspond to a reclining posture. Although not illustrated, the sensor 220 can also determine orientations along the lateral-medial axis of the body in order to detect postures such as lying on one's side.

It will be appreciated that the sensors 200, 220 illustrated in FIGS. 2A-D are provided for illustration. Those familiar with the relevant arts may be able to adapt alternate technologies to detect gravitational field and/or motion in order to determine patient posture. For example, orientation may be derived using position sensing technologies, Doppler reflections, laser inferometry, and the like. Posture measurements may not only include measurements of the patient's body to a fixed reference (e.g., the earth's surface) but with reference to other body parts. For example, relative orientation of the legs to the torso may be used to differentiate sitting upright with standing.

Figure 3A:
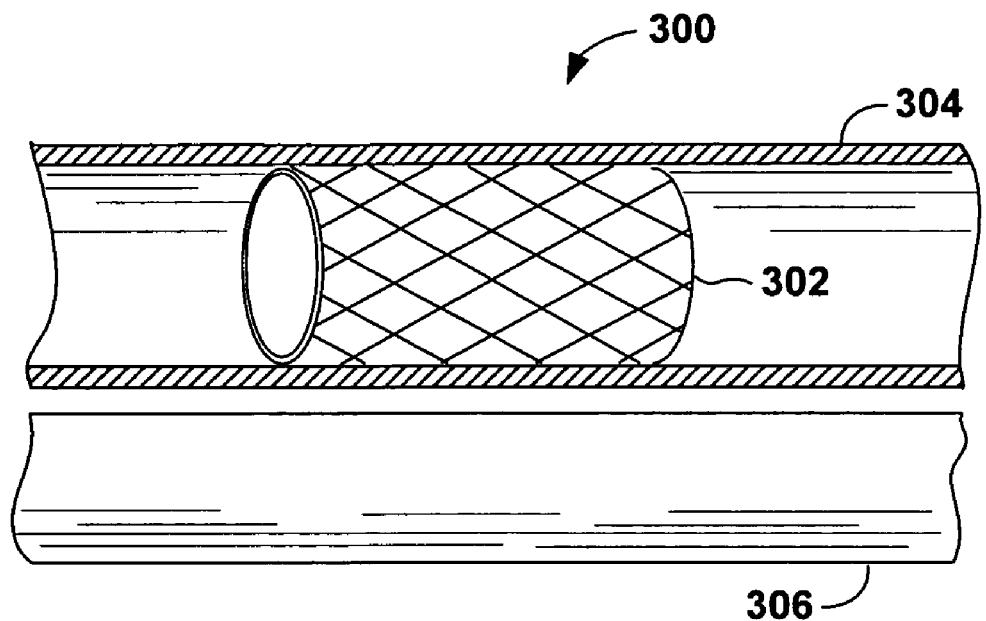
FIG. 3A is a side view illustrating a stent-like blood pressure sensing element according to an embodiment of the invention.
Figure 3B:
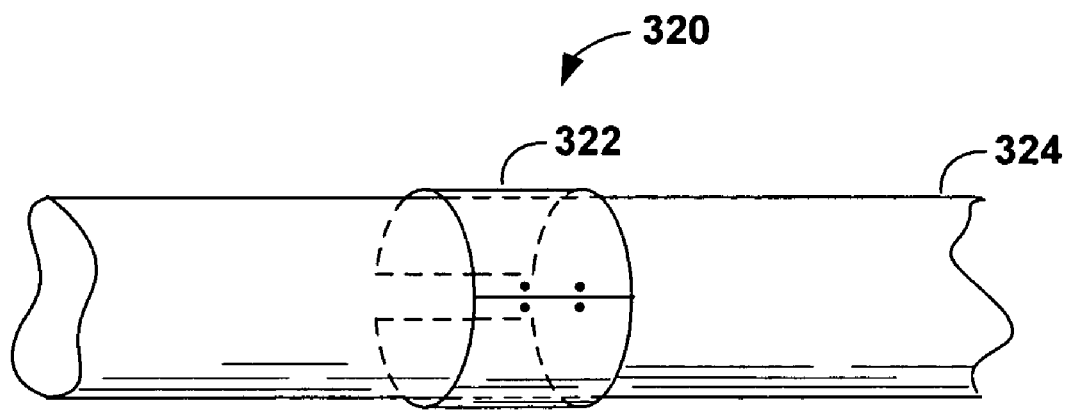
FIG. 3B is a side view illustrating a cuff transducer blood pressure sensor according to an embodiment of the invention.

The posture changes detected by posture sensors 200, 220 can be used as a trigger for measuring other physiological responses in order to determine autonomic imbalance. One of these physiological responses is the measurement of blood pressure. Example sensors that may be used for measuring blood pressure according to embodiments of the invention are shown in FIGS. 3A and 3B. FIG. 3A shows a transvenous sensor 300 that includes a stent-like element 302. The stent-like element 302 is placed inside a vein 304 that is paralleled by an artery 306. The stent transducer 302 can detect pressure changes via detecting the displacement or pulsatile movement induced by artery 306. A different, less invasive approach to determining blood pressure is shown in FIG. 3B, where a blood pressure sensor 320 includes an arterial cuff transducer 322 that is placed around an artery 324. The cuff transducer 322 may detect pressure based on expansion and contraction of the arterial wall.

Figure 4:
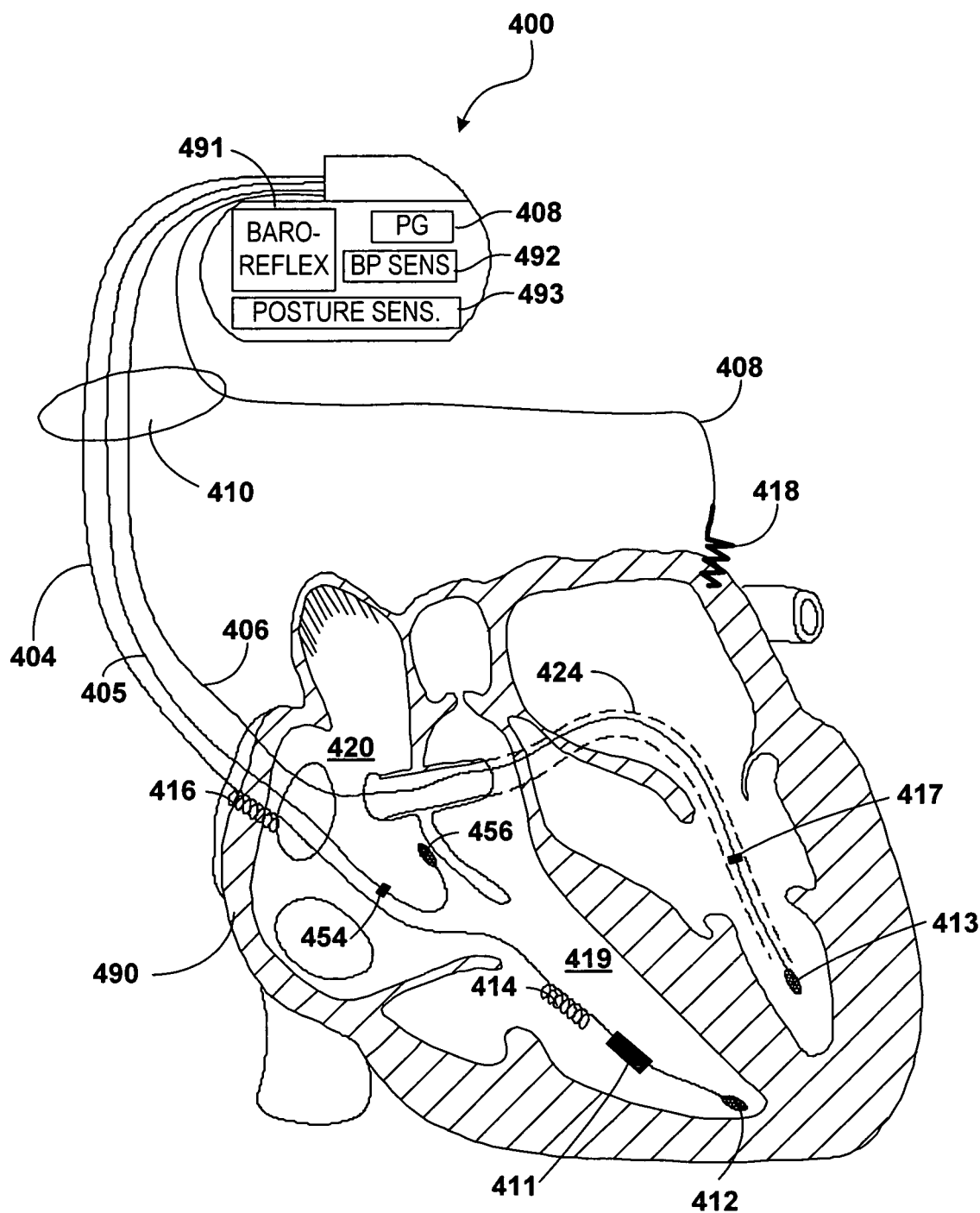
FIG. 4 is a block diagram and cutaway view illustrating an implantable device and lead system according to an embodiment of the invention.

Other physiological responses that can be measured following a posture change include electrical impulses of the heart. Referring now to FIG. 4 of the drawings, there is shown one embodiment of an implantable device 400 that may be used to measure cardiac electrical signals according to embodiments of the present invention. The implantable device 400 illustrated in FIG. 4 may include a baroreflex function analyzer 491, a blood pressure sensor 492, and a posture sensor 493 disposed within the can of the implantable device 400. The implantable device 400 may also include a cardiac pulse generator (PG) 408 that is electrically and physically coupled to a lead system 410.

The housing and/or header of the implantable device 400 may incorporate one or more electrodes used to provide electrical stimulation energy to the heart and to sense cardiac electrical activity. The electrodes may also be configured to detect electrical signals of the heart for purposes of detecting baroreflex indicators via the function analyzer 491. All or a portion of the implantable device housing may be configured as a can electrode. The implantable device 400 may include an indifferent electrode positioned, for example, on the header or the housing of the implantable device 400.

The lead system 410 is used to detect electrical signals produced by the heart 490 and may provide electrical energy to the heart 490 under certain predetermined conditions, such as to treat cardiac arrhythmias. The lead system 410 may include one or more electrodes used for pacing, sensing, and/or cardioversion/defibrillation. In the embodiment shown in FIG. 4, the lead system 410 includes an intracardiac right ventricular (RV) lead system 404, an intracardiac right atrial (RA) lead system 405, an intracardiac left ventricular (LV) lead system 406, and an extracardiac left atrial (LA) lead system 408. The lead system 410 of FIG. 4 illustrates one embodiment that may be used in connection with the multi level tachyarrhythmia therapy methodologies described herein. Other leads and/or electrodes may additionally or alternatively be used.

The lead system 410 may include intracardiac leads 404, 405, 406 implanted in a human body with portions of the intracardiac leads 404, 405, 406 inserted into a heart 490. The intracardiac leads 404, 405, 406 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 4, the lead system 410 may include one or more extracardiac leads 408 having electrodes, e.g., epicardial electrodes, positioned at locations outside the heart for sensing and/or pacing one or more heart chambers. The right ventricular lead system 404 illustrated in FIG. 6 includes an SVC-coil 416, an RV-coil 414, an RV-ring electrode 411, and an RV-tip electrode 412. The right ventricular lead system 404 extends through the right atrium 420 and into the right ventricle 419. In particular, the RV-tip electrode 412, RV-ring electrode 411, and RV-coil electrode 414 are positioned at appropriate locations within the right ventricle for sensing and delivering electrical stimulation pulses to the heart. The SVC-coil 416 is positioned at an appropriate location within the right atrium chamber of the heart 490 or a major vein leading to the right atrial chamber of the heart 490.

In one configuration, the RV-tip electrode 412 referenced to the can electrode may be used to implement unipolar pacing and/or sensing in the right ventricle 419. Bipolar pacing and/or sensing in the right ventricle may be implemented using the RV-tip 412 and RV-ring 411 electrodes. The RV-ring 411 electrode may optionally be omitted, and bipolar pacing and/or sensing may be accomplished using the RV-tip electrode 412 and the RV-coil 414, for example. Sensing in the RV may involve the tip-to-ring vector and the RV-coil to SVC-coil or the RV-coil to SVC coil electrically tied to the can vector. The right ventricular lead system 404 may be configured as an integrated bipolar pace/shock lead. The RV-coil 414 and the SVC-coil 416 are defibrillation electrodes.

The left ventricular lead 406 includes an LV distal electrode 413 and an LV proximal electrode 417 located at appropriate locations in or about the left ventricle for pacing and/or sensing the left ventricle. The left ventricular lead 406 may be guided into the right atrium 420 of the heart via the superior vena cava. From the right atrium 420, the left ventricular lead 406 may be deployed into the coronary sinus ostium, the opening of the coronary sinus. The lead 406 may be guided through the coronary sinus to a coronary vein 424 of the left ventricle. This vein is used as an access pathway for leads to reach the surfaces of the left ventricle that are not directly accessible from the right side of the heart. Lead placement for the left ventricular lead 406 may be achieved via subclavian vein access and a preformed guiding catheter for insertion of the LV electrodes 413, 417 adjacent to the left ventricle.

Unipolar pacing and/or sensing in the left ventricle may be implemented, for example, using the LV distal electrode 413 referenced to the can electrode. The LV distal electrode 413 and the LV proximal electrode 417 may be used together as bipolar sense and/or pace electrodes for the left ventricle. The left ventricular lead 406 and the right ventricular lead 404, in conjunction with the PG 408, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 405 includes a RA-tip electrode 456 and an RA-ring electrode 454 positioned at appropriate locations in the right atrium for sensing and pacing the right atrium. In one configuration, the RA-tip 456 referenced to the can electrode, for example, may be used to provide unipolar pacing and/or sensing in the right atrium 420. In another configuration, the RA-tip electrode 456 and the RA-ring electrode 454 may be used to achieve bipolar pacing and/or sensing.

FIG. 4 also illustrates one embodiment of a left atrial lead system 408. In this example, the left atrial lead 408 is implemented as an extracardiac lead with an LA distal electrode 418 positioned at an appropriate location outside the heart 490 for sensing and pacing the left atrium. Unipolar pacing and/or sensing of the left atrium may be accomplished, for example, using the LA distal electrode 418 to the can pacing vector. The left atrial lead 408 may be provided with additional electrodes used to implement bipolar pacing and/or sensing of the left atrium.

The cardiac signals detected from any of the leads 404, 405, 406, and 408 may be used as inputs to the baroreflex function analyzer 491. In an atrial and ventricular sensed arrangement, either atrial or ventricular signals can be used for heart rate changes for purposes of baroreflex sensitivity analysis. In a ventricular pacing arrangement where only atrial signals are sensed, atrial signals can be used for detecting heart rate changes.

Figure 5A:
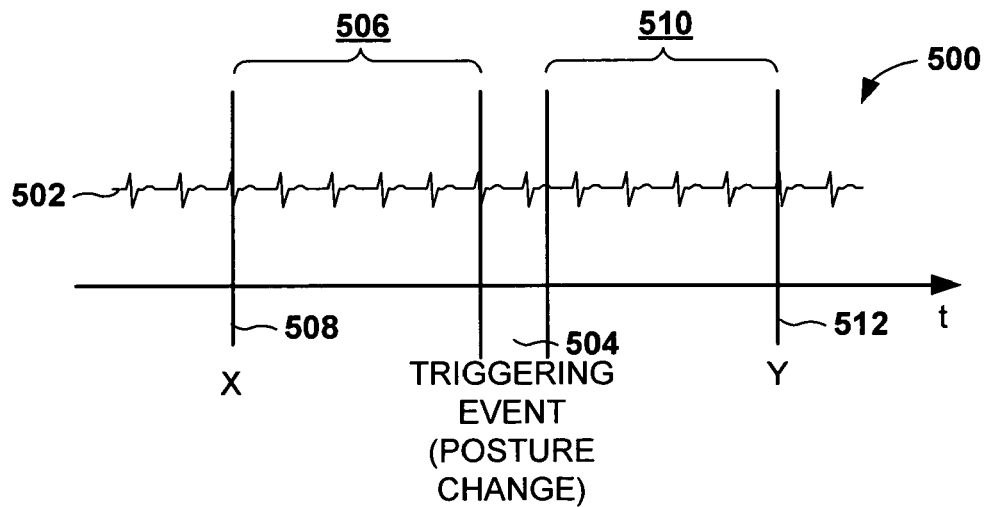
FIG. 5A is a time line diagram illustrating baroreflex sensitivity analysis (BSA) according to an embodiment of the invention.

In reference now to FIG. 5A, a graph 500 illustrates a data capture scheme for measuring baroreflex according to an embodiment of the invention. A series of signals 502 are continuously monitored via any combination of blood pressure sensors and cardiac signal sensors. A set of data representing the signals 502 is stored in a memory buffer or some other persistent or non-persistent data storage. A triggering event 504, here defined as a predefined change in posture, causes a baroreflex analysis to be performed. The triggering event 504 can be modeled as an instantaneous event, or as shown, as an event occurring over a finite period of time. The triggering event 504 causes the retrieval of a first set of data 506 that begins a time X 508 preceding the triggering event 504. In order to record data that precedes an unpredictable event, the relevant data that forms the data set 506 could be continuously captured (e.g., placed in a circular buffer), and when the triggering event 504 is detected, the data set 506 moved from the continuous buffer to a secondary memory buffer for purposes of performing calculations. The data set 506 (or other captured data) may also be moved to a persistent data storage for purposes such as building patient baseline data for physician view/retrieval and setting thresholds for a diagnostic alarm.

The signals 502 are also recorded after the trigger event 504 to determine a second set of data 510 that represents the state of the signals 502 after the trigger event 504 up until a time Y 512 after the event 504. The two sets of data 506, 510 can then be used to perform a baroreflex sensitivity analysis (BSA) to determine autonomic imbalance. The data occurring within the event 504 (assuming it is modeled as having non-zero duration) may also be used for the calculations. The times X 508 and Y 512 may be defined based on empirical analysis, and may be limited by such factors as available memory and processing speed of the measuring device. In one embodiment, the time X 508 may be about two minutes before the triggering event 504 and the time Y 512 may be about three minutes after the triggering event 504.

Figure 5B:
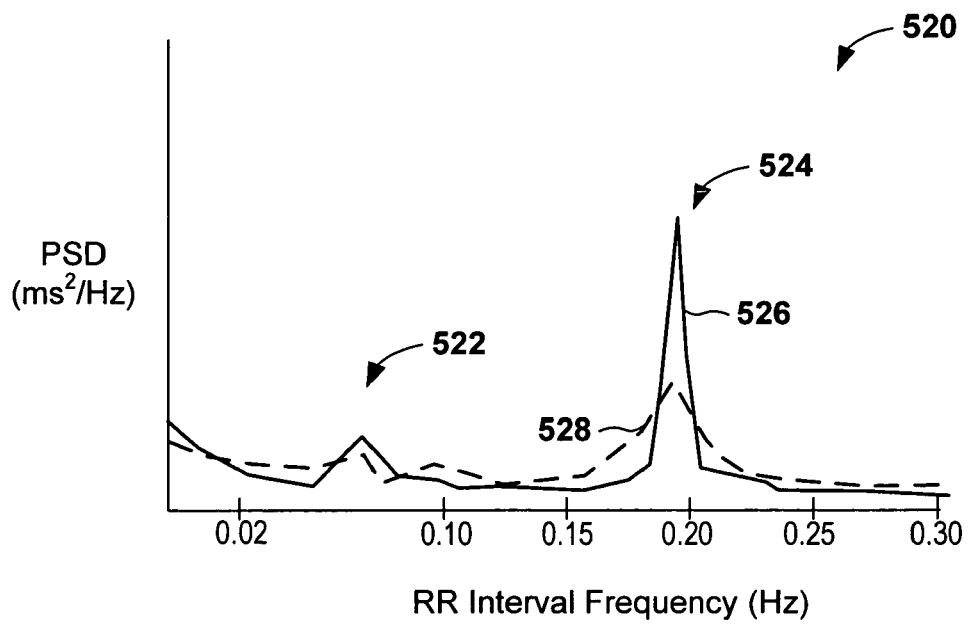
FIG. 5B is a graph illustrating BSA using a power spectrum plot of the R-R interval according to an embodiment of the invention.

After the data 506, 510 is gathered according to a scheme such as described in relation to FIG. 5A, it can be processed in a number of ways to determine various aspects of the baroreflex response. In reference now to FIG. 5B, a power spectrum plot 520 is shown illustrating heart rate variation according to an embodiment of the invention. The illustrated spectrum plot 520 contains may contain a number of components/features that can be used to characterize baroreflex. For example, a low frequency component 522 around 0.05 Hz may be regulated by vagus and cardiac sympathetic nerves. A high frequency component 524 around 0.20 Hz may be synonymous with respiration. The total power of the signal, integrated over all frequencies, is equal to the variance of the entire signal. The shape of the power spectrum 520 and/or discrete variables such as variance may be used to perform a baroreflex sensitivity analysis. For example, spectrum 528 has a flatter response around the characteristic frequencies 522, 524 compared to a spectrum 526 of a normal patient. Thus the spectrum 528 may indicative of autonomic imbalance.

Figure 6A:
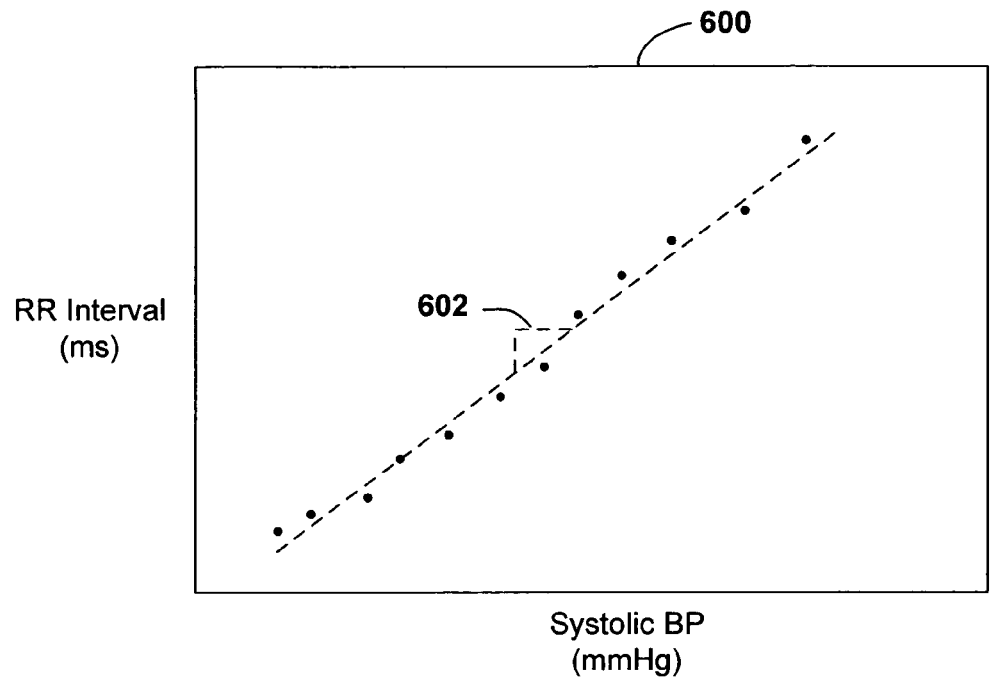
FIG. 6A is a graph illustrating BSA using blood pressure plotted versus the R-R interval according to an embodiment of the invention.

In reference now to FIG. 6A, another graph 600 illustrates a standard calculation of baroreflex sensitivity analysis using systolic blood pressure and the R-R interval according to an embodiment of the invention. The relationship between systolic blood pressure and the R-R interval is shown in FIG. 6A, where systolic blood pressure is plotted against the subsequent R-R interval during the period over which posture change is detected. The slope 602 of this relationship is calculated and used to analyze baroreflex sensitivity. Although FIG. 6A uses R-R interval for baroreflex sensitivity analysis, it will be appreciated that any appropriate heart rate interval may be used (e.g., A-A interval).

Although the method of determining baroreflex shown in FIG. 6A is effective, other methods may be more amenable to measurement via implantable devices. One novel approach for determining baroreflex sensitivity according to an embodiment of the invention is shown in the graph 610 of FIG. 6B. In this graph 610, the patient's R-R interval is plotted as a function of time. Posture change is a trigger of the baroreflex. The baroreflex sensitivity is determined as the slope 612 of this plot in a time period roughly corresponding to change in posture.

Figure 6B:
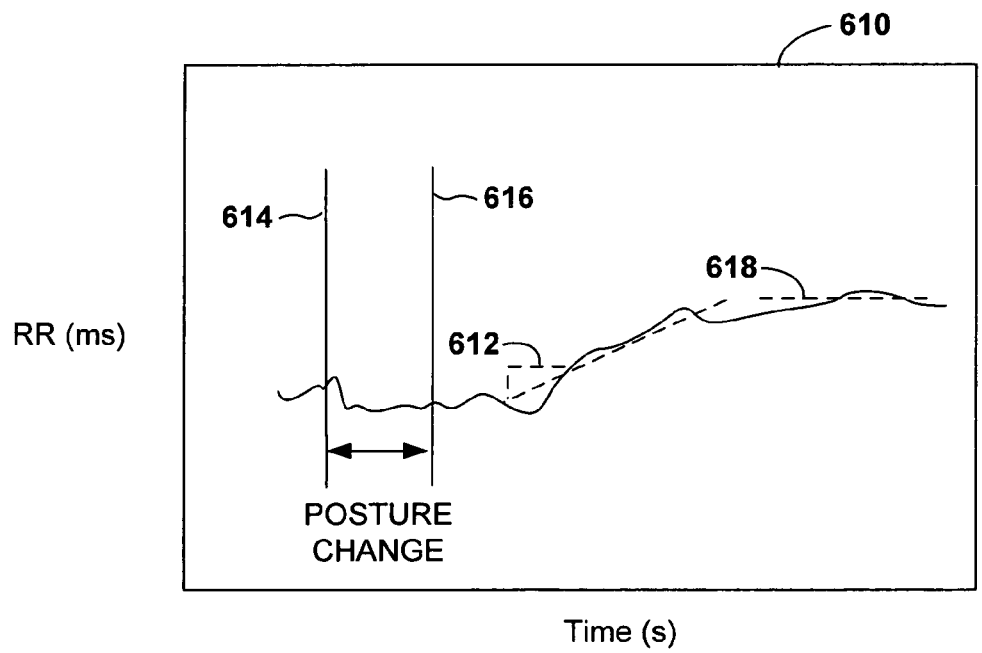
FIG. 6B is a graph illustrating BSA using the time rate of change of the R-R interval according to an embodiment of the invention.

The change in posture is represented in FIG. 6B by time values 614 and 616. The blood pressure and heart rate changes occur at a time beyond the posture change itself 614, 616. Typically, the posture change 614, 616 takes 1 or 2 seconds, and blood pressure decrease starts after the posture change (e.g., after time 616). The baroreflex analysis will generally monitor blood pressure and heart rate for some period of time after the posture change 614, 616 is complete. For example, measurements may be taken until a plateau 618 is measured. Thereafter, the data captured preceding the plateau 618 and after (or near) the completion of posture change 616 can be used to calculate the slope 612 to determine baroreflex sensitivity.

Figure 7:
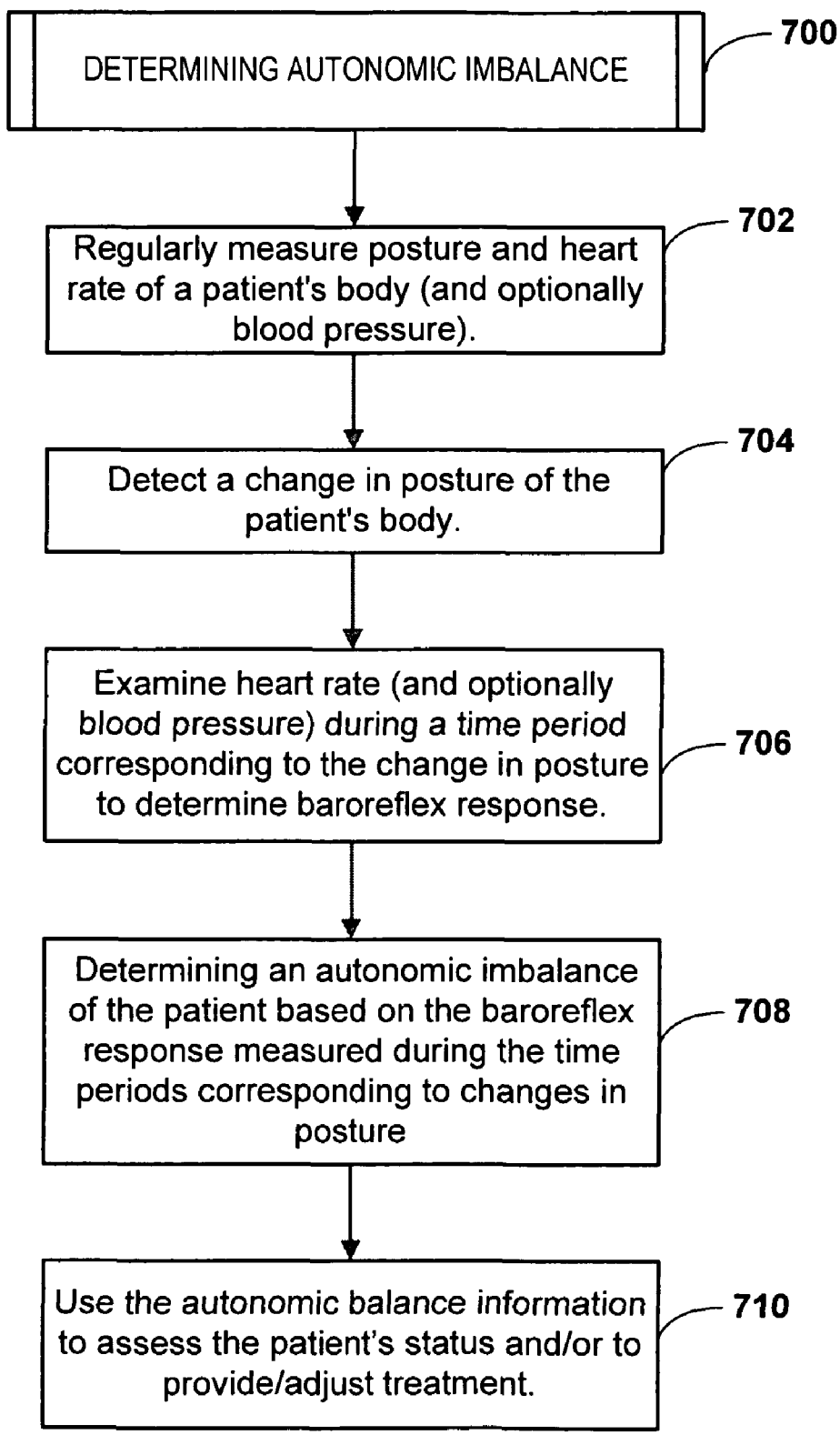
FIG. 7 is a flowchart illustrating a procedure for determining autonomic imbalance according to an embodiment of the invention.

In reference now to FIG. 7, a procedure 700 is illustrated for determining an autonomic disorder according to an embodiment of the present invention. The procedure 700 involves regularly measuring 702 posture heart rate (e.g. cardiac signals) of a patient's body. These measurements 702 may also include blood pressure, and are typically made via an integrated, implantable device, although other devices may also be used for some or all of the measurements. During the measurement 702, a change in posture is detected 704 in the patient's body, typically involving a change in orientation of the torso.

When the change is detected 704, a baroreflex response is determined 706 based on data captured during a time period corresponding to the change in posture 704. The time period may encompass readings made before the posture change 704 and/or after the posture change 704. This determination 706 may include a baroreflex sensitivity analysis (BSA), and use any combination of techniques, including R-R spectral analysis, rate of change of systolic blood pressure relative to R-R intervals, and time rate of change of R-R intervals during the change in posture 704. Any baroreflex responses so determined 706 may be used to determine 708 autonomic imbalances. The autonomic imbalances detected 708 may then be used 710 to assess patient status and to provide for or adjust treatment.

Figure 8:
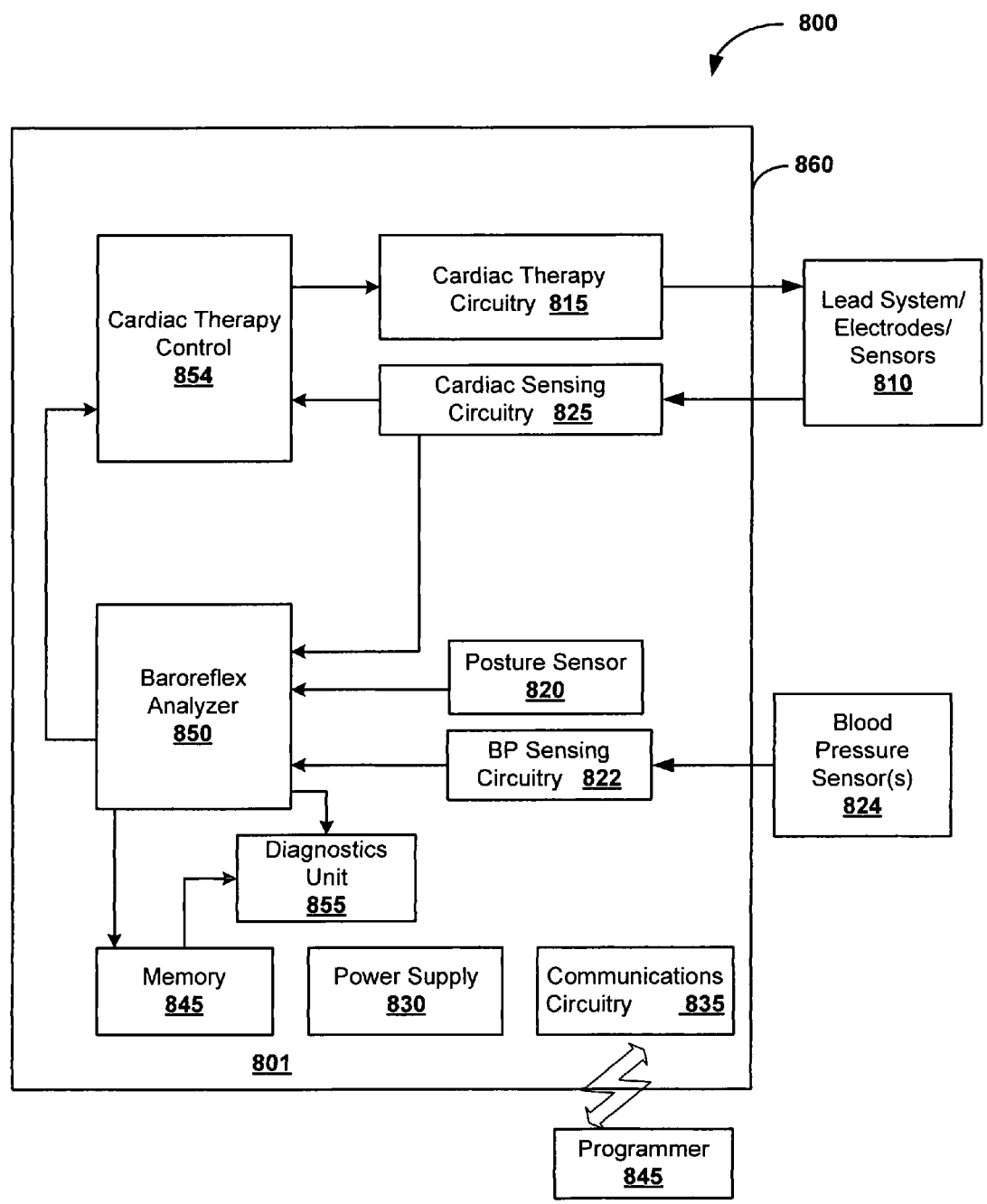
FIG. 8 is a block diagram of an implantable device according to an embodiment of the invention.

Referring now to FIG. 8, there is shown a block diagram of an implantable device 800 suitable for implementing baroreflex sensitivity and autonomic imbalance determinations according to an embodiment of the present invention. FIG. 8 shows the implantable device 800 divided into functional blocks. There exist many possible configurations in which these functional blocks can be arranged. The example depicted in FIG. 8 is one possible functional arrangement. The implantable device 800 depicted in FIG. 8 includes CRM circuitry including cardiac sensing circuitry for receiving cardiac signals from a heart and delivering electrical energy in the form of pace pulses or cardioversion/defibrillation pulses to the heart.

The housing 860 of the implantable device 800 encloses a single- or multi-axis posture sensor assembly 820. The posture sensor 820 may include any combination of piezoelectric elements, ball and cup tilt sensors, mechanical tilt sensors, DC accelerometers, AC accelerometers, or any other posture sensor known in the art. The sensor assembly 820 may also have other internal or external signal conditioning circuitry (not shown) such as high pass and low pass filters.

The implantable device 800 also includes a blood pressure sensing assembly 822 that is coupled to blood pressure sensors 824. The blood pressure sensors 824 may include any combination of stent sensors, cuff sensors, or other blood pressure sensing technologies known in the art. The implantable device 800 also includes cardiac sensing circuitry 825 used to detect cardiac electrical signals via sensors such as implantable electrodes.

The outputs of the cardiac sensing circuitry 825, blood pressure sensing circuitry 822, and posture sensor 820, are coupled to a baroreflex analyzer 850. The baroreflex analyzer 850 may be used to determine autonomic imbalance in accordance with methodologies of the present invention described herein. For example, the baroreflex analyzer 850 may make determination of autonomic imbalance using baroreflex sensitivity analysis (BSA).

The baroreflex analyzer 850 may be implemented using general-purpose, programmable microprocessors or custom digital and/or analog circuitry. The baroreflex analyzer 850 may be able to access registers of a memory 845 for storing and retrieving data of interest, including measurements of dynamic or mean blood pressures, cardiac signal waveforms, R-R intervals, posture, etc. The baroreflex analyzer 850 may include circuitry and/or instructions for performing various functions known in the art that are applicable to the present invention. For example, the posture processor 850 may include digital signal processing (DSP) logic for performing spectral analysis on R-R intervals measured before and after posture change trigger events.

In the embodiment illustrated in FIG. 8, the baroreflex analyzer 850, posture sensor 820, blood pressure sensing circuitry 822, and calibration circuitry 840 are disposed within the housing 860 of the implantable device 800 along with CRM circuitry. A cardiac lead system 810 may be implanted so that cardiac electrodes are electrically coupled to the heart tissue as described above in connection with FIG. 4. The cardiac electrodes of the lead system 810 along with sensing circuitry 825 disposed within the implantable device housing are used to sense cardiac signals associated with electrical activity of the heart.

The cardiac electrodes and lead system 810 may also be used to deliver electrical stimulation pulses or shocks generated by the cardiac therapy circuitry 815 to the heart for treating various cardiac arrhythmias. The CRM circuitry, including the therapy control circuitry 854, cardiac sensing circuitry 825, cardiac therapy circuitry 815, and cardiac electrodes/lead system 810, may detect cardiac signals and deliver therapeutic electrical stimulation to any of the left and right ventricles and left and right atria, for example. In some implementations, the therapy control circuitry may use posture and/or BSA information to modify therapy delivered to the patient.

Power to the implantable device 860 is supplied by an electrochemical battery 830 that is housed within the implantable device 860. The implantable device 860 may also include various forms of memory 845. The memory 845 may be used to store sensor information for tracking changes in patient autonomic tone over time. In some implementations, the implantable device 860 may incorporate a diagnostics processor 855 that utilizes autonomic information stored in memory 840, possibly along with other information, to detect the presence or track the progression of various medical disorders. In another implementation, the diagnostics processor is incorporated in a remote patient external device. The posture information, along with other parameters and data stored in the memory 840, may be transmitted via telemetry to an external programmer unit 845 or other patient-external device, as desired.

Communications circuitry 835 allows the implantable device 860 to communicate with an external programmer unit 845 and/or other patient-external system(s). In one embodiment, the communications circuitry 835 and the programmer unit 845 use a wire loop antenna and a radio frequency telemetric link to receive and transmit signals and data between the programmer 845 and communications circuitry 835. In this manner, programming commands and/or other information may be transferred to the implantable device 860 from the programmer 845 during and after implant.

A number of the examples presented herein involve block diagrams illustrating functional blocks used for in accordance with embodiments of the present invention. It will be understood by those skilled in the art that there exist many possible configurations in which these functional blocks can be arranged and implemented.

The examples depicted herein provide examples of possible functional arrangements used to implement the approaches of the invention. The components and functionality depicted as separate or discrete blocks/elements in the figures in general can be implemented in combination with other components and functionality. The depiction of such components and functionality in individual or integral form is for purposes of clarity of explanation, and not of limitation. It is also understood that the components and functionality depicted in the Figures and described herein can be implemented in hardware, software, or a combination of hardware and software.

Methods, devices, and systems in accordance with the present invention may incorporate one or more of the features, structures, methods, or combinations thereof described herein. For example, a medical system may be implemented to include one or more of the features and/or processes described herein. It is intended that such a method, device, or system need not include all of the features and functions described herein, but may be implemented to include one or more selected features and functions that provide unique structures and/or functionality.

Various modifications and additions can be made to the embodiments discussed hereinabove without departing from the scope of the present invention. Further, although the present description is related to medical device uses, it will be appreciated that similar sensing circuitry may be used in other medical, industrial, or military applications that may require the measurement of device orientation. Accordingly, the scope of the present invention should not be limited by the particular embodiments described above, but should be defined only by the claims set forth below and equivalents thereof.

What is claimed is:

1. An apparatus capable of being implanted in a patient's body, comprising:
   a posture sensor;
   a source of blood pressure data;
   a heart rate sensor; and
   a processor coupled to the posture sensor and the heart rate sensor, the processor configured to:
      measure the patient's heart rate via the heart rate sensor;
      detect a change in a posture of the patient's body via the posture sensor; and
      determine an autonomic tone of the patient's body based on the patient's heart rate measured during a time period corresponding to the change in posture;
   wherein the processor is configured to determine the autonomic tone by performing a baroreflex sensitivity analysis (BSA) based on the heart rate and blood pressure measured during the time period; and
   wherein performing the BSA comprises determining a rate of change of systolic blood pressure relative to heart beat intervals during the time period corresponding to the change in posture.

2. The apparatus of claim 1, wherein the source of blood pressure data comprises a blood pressure sensor, and wherein the processor is further configured to measure the patient's blood pressure via the blood pressure sensor.

3. The apparatus of claim 2, wherein the blood pressure sensor comprises a force transducer sensitive to displacement of a blood vessel.

4. The apparatus of claim 3, wherein the force transducer comprises a stent-like element capable of being implanted within a blood vessel of the patient's body.

5. The apparatus of claim 3, wherein the force transducer comprises a cuff transducer capable of being placed around a blood vessel.

6. The apparatus of claim 2, wherein one or more of the posture sensor, heart rate sensor, and blood pressure sensor are self-contained within the implantable apparatus.

7. The apparatus of claim 2, wherein one or more of the posture sensor, heart rate sensor, and blood pressure sensor are configured to work in conjunction with an external apparatus.

8. The apparatus of claim 1, wherein the posture sensor comprises at least one of a piezoelectric sensor and an accelerometer.

9. The apparatus of claim 1, wherein the posture sensor comprises:
   a case having a plurality of conductive surfaces disposed on an inner surface of the case; and
   a conductive solid movably disposed along the inner surface of the case, wherein movement of the conductive solid within the case causes the conductive solid to create an electrical connection between at least two surfaces of the plurality of surfaces.

10. The apparatus of claim 1, wherein the processor is configured to determine the autonomic tone by performing a baroreflex sensitivity analysis (BSA) based on the heart rate signals measured during the time period.

11. The apparatus of claim 1, further comprising a housing in which one or more of the posture sensor, the heart rate sensor, and the processor is disposed, the housing being adapted for implantation in a thoracic region of the patient.

12. The apparatus of claim 1, wherein the posture sensor is adapted to sense only relative changes in posture.

13. The apparatus of claim 1, wherein the posture sensor is adapted to sense absolute orientations.

14. An apparatus capable of being implanted in a patient's body, comprising:
   a posture sensor;
   a heart rate sensor; and
   a processor coupled to the posture sensor and the heart rate sensor, the processor configured to:
      measure the patient's heart rate via the heart rate sensor;
      detect a change in a posture of the patient's body via the posture sensor; and
      determine an autonomic tone of the patient's body based on the patient's heart rate measured during a time period corresponding to the change in posture;
   wherein the processor is configured to determine the autonomic tone by performing a baroreflex sensitivity analysis (BSA) based on the heart rate signals measured during the time period; and
   wherein the processor is configured to perform the BSA based on a power spectral analysis of heart beat intervals determined via the heart rate sensor.

15. An apparatus capable of being implanted in a patient's body, comprising:
   a posture sensor;
   a heart rate sensor; and
   a processor coupled to the posture sensor and the heart rate sensor, the processor configured to:
      measure the patient's heart rate via the heart rate sensor;
      detect a change in a posture of the patient's body via the posture sensor; and
      determine an autonomic tone of the patient's body based on the patient's heart rate measured during a time period corresponding to the change in posture;
   wherein the processor is configured to determine the autonomic tone by performing a baroreflex sensitivity analysis (BSA) based on the heart rate signals measured during the time period; and
   wherein the processor is configured to perform the BSA based on a time rate of change of heart beat intervals during the time period corresponding to the change in posture.

16. The apparatus of claim 15, further comprising an electrode for coupling to the heart rate sensor, the electrode being adapted for intracardiac placement.

17. The apparatus of claim 15, further comprising a first memory for temporarily storing heart rate information from the heart rate sensor.

18. The apparatus of claim 17, further comprising a second memory, wherein the apparatus is configured to move the stored heart rate information from the first memory to the second memory in response to a triggering event sensed by the posture sensor.

19. The apparatus of claim 15, wherein the posture sensor comprises at least one of a piezoelectric sensor and an accelerometer.

20. The apparatus of claim 15, wherein the posture sensor comprises:
   a case having a plurality of conductive surfaces disposed on an inner surface of the case; and
   a conductive solid movably disposed along the inner surface of the case, wherein movement of the conductive solid within the case causes the conductive solid to create an electrical connection between at least two surfaces of the plurality of surfaces.

* * * * *